(12) United States Patent
Campeau-Lecours et al.

(10) Patent No.: US 12,257,167 B2
(45) Date of Patent: Mar. 25, 2025

(54) MOVEMENT ASSISTANCE APPARATUS, E.G., FOR FEEDING, WRITING

(71) Applicant: UNIVERSITE LAVAL, Quebec (CA)

(72) Inventors: Alexandre Campeau-Lecours, Quebec (CA); Philippe Turgeon, Quebec (CA); François Routhier, Quebec (CA); Thierry Laliberte, Quebec (CA)

(73) Assignee: UNIVERSITE LAVAL, Quebec (CA)

( * ) Notice: Subject to any disclaimer, the term of this patent is extended or adjusted under 35 U.S.C. 154(b) by 999 days.

(21) Appl. No.: 17/272,707

(22) PCT Filed: Sep. 5, 2019

(86) PCT No.: PCT/CA2019/051241
§ 371 (c)(1),
(2) Date: Mar. 2, 2021

(87) PCT Pub. No.: WO2020/047666
PCT Pub. Date: Mar. 12, 2020

(65) Prior Publication Data
US 2021/0369478 A1    Dec. 2, 2021

Related U.S. Application Data

(60) Provisional application No. 62/770,791, filed on Nov. 22, 2018, provisional application No. 62/727,713, filed on Sep. 6, 2018.

(51) Int. Cl.
*A61F 4/00*    (2006.01)
*B25J 1/02*    (2006.01)

(52) U.S. Cl.
CPC .. *A61F 4/00* (2013.01); *B25J 1/02* (2013.01)

(58) Field of Classification Search
CPC .... A61F 4/00; B25J 1/02; B25J 9/0009; B25J 9/0021
See application file for complete search history.

(56) References Cited

U.S. PATENT DOCUMENTS 3,885,681 A * 5/1975 Mancino ............... A47G 21/08
                                                    414/9
4,218,167 A * 8/1980 Mansfield ............. A47G 21/08
                                                    414/9

(Continued)

FOREIGN PATENT DOCUMENTS

AU    2016250360 A1    5/2018
CN    101081184 A      12/2007

(Continued)

*Primary Examiner* — Saul Rodriguez
*Assistant Examiner* — Brendan P Tighe
(74) *Attorney, Agent, or Firm* — NORTON ROSE FULBRIGHT CANADA LLP

(57) ABSTRACT

An apparatus comprises a main arm having links extending from a ground end to an effector end and allowing movement of the effector end from a first position to a second position, the links including at least a base link adapted to be pivotally connected to a base, and a spacing link pivotally mounted to a free end of the base link and extending to the effector end. A first 4-bar parallelogram has pivot joints at its corners and including the base link of the main arm. A second 4-bar parallelogram has pivot joints at its corners and including the spacing link of the main arm and an effector link at the effector end adapted to support an object. A serial interconnection is between the first 4-bar parallelogram and the second 4-bar parallelogram constraining the effector link to maintaining a constant orientation in at least two rotational degrees of freedom relative to the base.

20 Claims, 9 Drawing Sheets

(56) References Cited

U.S. PATENT DOCUMENTS

| | | | |
|---|---|---|---|
| 5,282,711 A * | 2/1994 | Frische | A47G 23/0225 |
| | | | 414/9 |
| 2013/0090756 A1 | 4/2013 | Dekar | |
| 2016/0109056 A1 | 4/2016 | Chen et al. | |
| 2016/0220404 A1 * | 8/2016 | Fogelberg | A61F 4/00 |
| 2016/0346940 A1 * | 12/2016 | Bax | A61B 34/30 |

FOREIGN PATENT DOCUMENTS

| | | | | |
|---|---|---|---|---|
| CN | 106 737 601 A | | 5/2017 | |
| EP | 1 863 734 A2 | | 12/2007 | |
| GB | 2555928 A | | 5/2018 | |
| JP | 2010058184 A | | 3/2010 | |
| KR | 20170012631 A | * | 2/2017 | |
| KR | 101787265 B1 | * | 10/2017 | |
| KR | 20200145398 A | * | 12/2020 | |
| WO | WO-2015053700 A1 | * | 4/2015 | A61F 4/00 |

* cited by examiner

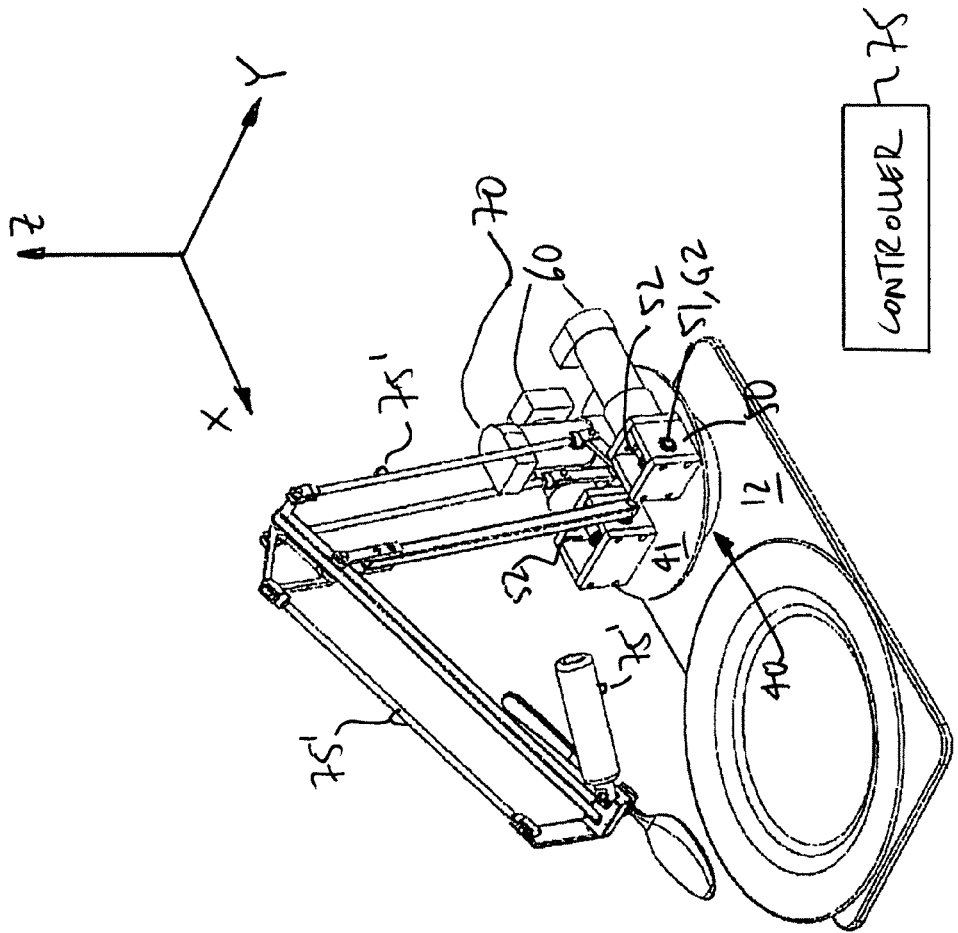
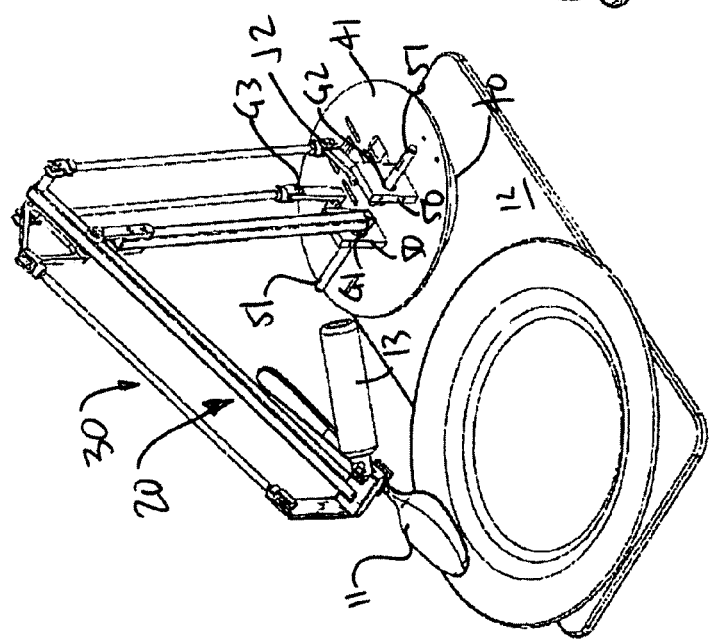
FIG. 4
FIG. 3

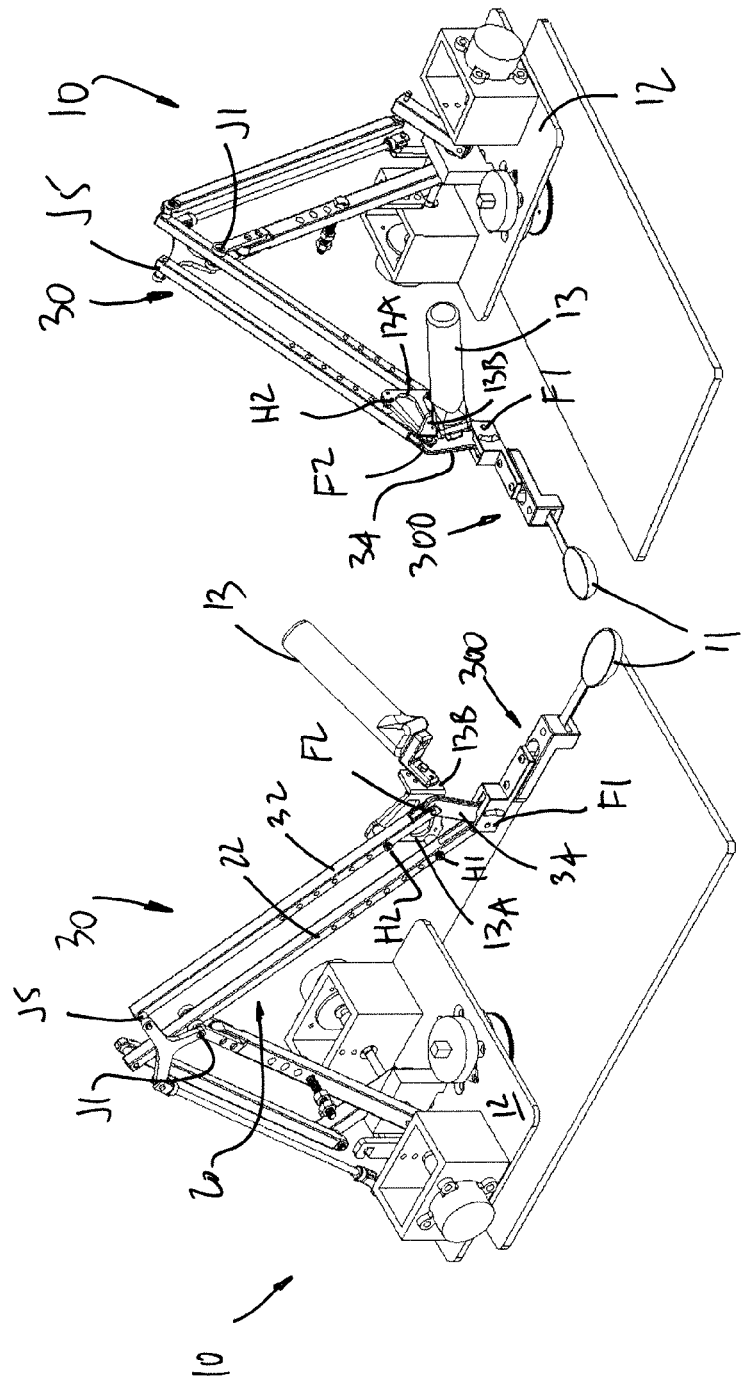

MOVEMENT ASSISTANCE APPARATUS, E.G., FOR FEEDING, WRITING

CROSS-REFERENCE TO RELATED APPLICATION

The present application claims the priorities of U.S. patent application Ser. No. 62/727,713, filed on Sep. 6, 2018, and of U.S. patent application Ser. No. 62/770,791, filed on Nov. 22, 2018, both of which are incorporated herein by reference.

TECHNICAL FIELD

The present application relates to assistive robots and mechanisms.

BACKGROUND OF THE ART

Some tasks performed routinely by healthy subjects may prove difficult for people with given ailments or conditions. For example, tasks such as feeding oneself may be challenging for people having limited range of arm movements or motor control deficiencies (spasms, tremors) through various injuries, diseases and ailments. This results in the use of resources for feeding tasks, notably caregivers.

Assistive robots have therefore been developed to perform such tasks. Some assistive robots are not only capable of performing such tasks, but also others, by having robotic arms actuated in multiple degrees of freedom through sizable volumes of operation. While such assistive robots and mechanisms may succeed in performing such tasks, they may not be cost effective due to their complex constructions related to the multiple tasks they may be capable of achieving. Moreover, assistive robots and mechanisms often operate in a fully autonomous mode, and some tasks may be lengthy as a result of assistive robot latency. It would therefore be desirable to develop an assistive mechanism that would complement human maneuvers or manipulations with assistive forces and constraints, in a collaborative manner.

SUMMARY

It is an aim of the present disclosure to provide an assistive apparatus that addresses issues related to the prior art.

It is an aim of the present disclosure to provide such an assistive apparatus for manual tasks such as feeding or writing, among others.

In accordance with an embodiment of the present disclosure, there is provided an apparatus comprising: a main arm having links extending from a ground end to an effector end and allowing movement of the effector end from a first position to a second position, the links including at least a base link adapted to be pivotally connected to a base, and a spacing link pivotally mounted to a free end of the base link and extending to the effector end; a first 4-bar parallelogram having pivot joints at its corners and including the base link of the main arm; a second 4-bar parallelogram having pivot joints at its corners and including the spacing link of the main arm and an effector link at the effector end adapted to support an object; and a serial interconnection between the first 4-bar parallelogram and the second 4-bar parallelogram constraining the effector link to maintaining a constant orientation in at least two rotational degrees of freedom relative to the base.

Further in accordance with the embodiment, for instance, further comprising a drive link assembly between the spacing link of the second 4-bar mechanism and the base.

Still further in accordance with the embodiment, for instance, the drive link assembly includes a first link and a second link pivotally interconnected to one another.

Still further in accordance with the embodiment, for instance, the first link is pivotally connected to the ground, and the second link is pivotally connected to the spacing link.

Still further in accordance with the embodiment, for instance, the first link and the base link are coaxially pivotally connected to the ground.

Still further in accordance with the embodiment, for instance, a portion of the spacing link extends beyond one said pivot joint of the second 4-bar parallelogram, the drive link assembly being connected to said portion of the spacing link.

Still further in accordance with the embodiment, for instance, the serial interconnection includes a single joining link forming a bar of the first 4-bar parallelogram and a bar of the second 4-bar parallelogram, and pivotally connected to a joint connecting the free end of the base link to the spacing link.

Still further in accordance with the embodiment, for instance, a plane in which lies the first and second 4-bar mechanisms is transverse to the base.

Still further in accordance with the embodiment, for instance, a plane in which lies the first and second 4-bar mechanisms is parallel to the base.

Still further in accordance with the embodiment, for instance, a turntable may be provided between the base and the ground.

Still further in accordance with the embodiment, for instance, a handle may be connected to the second 4-bar mechanism.

Still further in accordance with the embodiment, for instance, a handle link may be interfacing the handle to the second 4-bar mechanism.

Still further in accordance with the embodiment, for instance, the handle link is pivotally connected to the second 4-bar mechanism and parallel to two bars of the second 4-bar mechanism.

Still further in accordance with the embodiment, for instance, a bracket portion may be on the handle link, the handle connected to the bracket portion.

Still further in accordance with the embodiment, for instance, the bracket portion is transverse to a plane of the 4-bar mechanisms.

Still further in accordance with the embodiment, for instance, the handle is rotatably connected to the bracket portion by a rotational joint.

Still further in accordance with the embodiment, for instance, a utensil may be connected to the effector link.

Still further in accordance with the embodiment, for instance, a utensil interface may be between the utensil and the effector link.

Still further in accordance with the embodiment, for instance, the utensil interface is connected to the second 4-bar mechanism by a lockable rotational joint.

Still further in accordance with the embodiment, for instance, the utensil interface has a lockable translation joint between the effector link and the utensil.

Still further in accordance with the embodiment, for instance, the utensil interface has a resilient member between the effector link and the utensil.

Still further in accordance with the embodiment, for instance, a first actuator may be operatively connected to the base link to actuate a pivot connection of the base link to the base.

Still further in accordance with the embodiment, for instance, further a second actuator may be operatively connected to the drive link assembly to actuate a pivot connection of the drive link assembly to the base.

Still further in accordance with the embodiment, for instance, at least one of the first actuator and the second actuator is a bidirectional motor.

Still further in accordance with the embodiment, for instance, a manual driving transmission may be operatively connected to the base link to actuate a pivot connection of the base link to the base, and operatively connected to the drive link assembly to actuate a pivot connection of the drive link assembly to the base.

Still further in accordance with the embodiment, for instance, the manual driving transmission includes a set of gears intermeshed to couple the pivot connection of the base link to the base with the pivot connection of the drive link assembly to the base.

Still further in accordance with the embodiment, for instance, the manual driving transmission includes a rack with handle meshed to the set of gears, whereby a translation of the rack results in movement of the effector link.

Still further in accordance with the embodiment, for instance, a writing instrument interface may be at the effector link.

In accordance with another embodiment of the present disclosure, there is provided a system comprising the apparatus as described above; at least one sensor producing signals indicative of movement of the apparatus; a processing unit; and a non-transitory computer-readable memory communicatively coupled to the processing unit and comprising computer-readable program instructions executable by the processing unit for: obtaining and interpreting the signals; identifying unwanted forces applied to the apparatus from the signals; and driving the first actuator and/or the second actuator for the effector link to offset the unwanted forces.

Still further in accordance with the embodiment, for instance, the computer-readable program instructions executable by the processing unit are further for driving the first actuator and/or the second actuator to assist in moving the apparatus.

Still further in accordance with the embodiment, for instance, the computer-readable program instructions executable by the processing unit are further for driving the first actuator and/or the second actuator to create inertia in the apparatus.

In accordance with another embodiment of the present disclosure, there is provided an apparatus comprising: a main arm having links extending from a ground end to an effector end and actuatable for movement of the effector end from a first position to a second position, the links including a base link adapted to be pivotally mounted to a ground, and a spacing link pivotally mounted to a free end of the base link and extending to the effector end; a first 4-bar parallelogram having pivot joints at its corners and including the base link of the main arm; and a second 4-bar parallelogram having pivot joints at its corners and including the spacing link of the main arm and an effector link adapted to support an object; wherein the first 4-bar parallelogram and the second 4-bar parallelogram are serially interconnected whereby the effector link is constrained to maintaining a constant orientation in at least two rotational degrees of freedom.

DESCRIPTION OF THE DRAWINGS

FIG. 3 is a perspective view of the feeding assistance apparatus of FIG. 1, showing a ground mounting configuration;

FIG. 4 is a perspective view of the feeding assistance apparatus of FIG. 3, with actuators or dampers;

FIG. 9 is a first perspective view of a feeding assistance apparatus, with a handle and utensil interface in accordance with another embodiment;

FIG. 10 is a second perspective view of the feeding assistance apparatus of FIG. 9;

DETAILED DESCRIPTION

Figure 1:
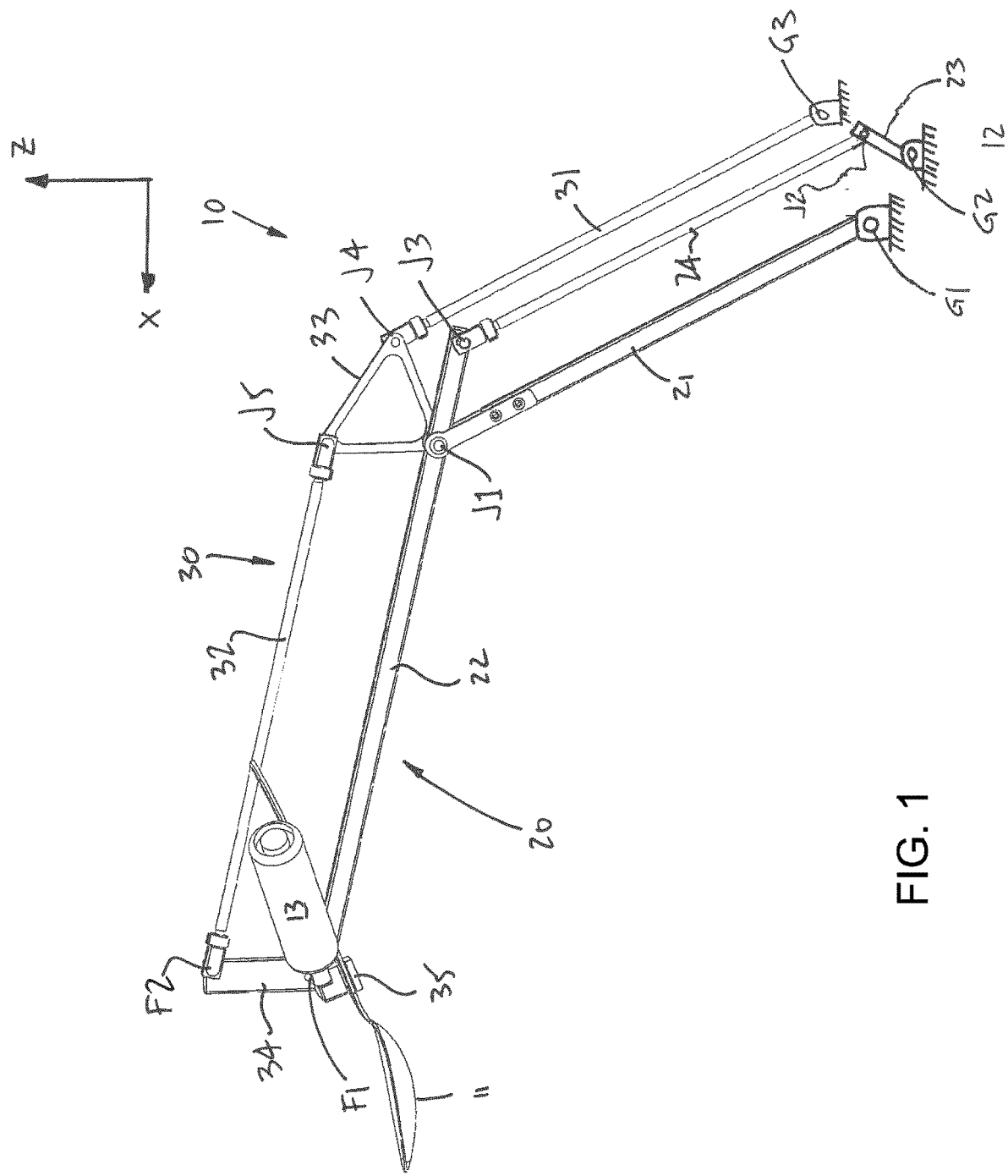
FIG. 1 is a perspective view of a feeding assistance apparatus in accordance with the present disclosure.

Referring to the drawings and more particularly to FIG. 1, a movement assistance apparatus in accordance with the present disclosure is generally shown at 10. To assist in describing it, the movement assistance apparatus 10 is shown as being a feeding assistance apparatus and described as such in the following paragraphs, though this is an exemplary use among others. However, the movement assistance apparatus 10 may be used in numerous other tasks. The feeding assistance apparatus 10 is of the type that may be used to assist a user during a feeding action, such as bringing a spoon to one's mouth. The feeding assistance apparatus 10 is configured for self-feeding, such that the typical user can autonomously feed oneself, with the assistance of the apparatus 10. For instance, the feeding assistance apparatus 10 may be used by physically impaired users, such as people having temporary or permanent disabilities, injuries or ailments, elderly users in loss of autonomy, among other examples. The feeding assistance apparatus 10 may also be used by people without disabilities as well. The apparatus 10 could be a robot arm, and may also be referred to as a manipulator.

According to an embodiment, the feeding assistance apparatus 10 is used with a utensil 11 such as a spoon as in FIG. 1, as the feeding assistance apparatus 10 has the property of maintaining an orientation of the utensil 11 constant relative to the ground 12. In an embodiment, the constant orientation is relative to an axis normal to a plane in which the 4-bar parallelograms of the apparatus 10 lie, as described below. The expression "ground" is used generically to represent a surface, mechanism or structure supporting the feeding assistance apparatus 10. The "ground" may for example be a table, a wheelchair, etc, and may also include mechanisms such as a turntable described hereinafter. With respect to the referential X,Y,Z of FIG. 1 (axis Y normal to the plane of the sheet of FIG. 1), the orientation of the utensil 11 is fixed relative to the plane XY (with the XY plane fixed relative to the ground 12). In an embodiment, the utensil 11 may rotate about axis Z, but in doing so the horizontality of the utensil 11 is preserved. Accordingly, with an orientation fixed in at least axes X and Y, the spoon 11 may scoop a liquid, and maintain it until reaching one's mouth. Other utensils and items may be manipulated using the feeding assistance apparatus 10 as well, including a glass filled with liquid, a writing instrument such as a pencil, etc, as discussed hereinafter. A handle 13 may optionally be present, which handle 13 is ergonomically oriented for the user to operate the movements of the feeding assistance apparatus 10 in moving the utensil 11 from a plate to her/his mouth. The orientation of the handle 13 could be adjusted and locked into an orientation, depending on the tool it will support (e.g., a pencil may have a different orientation than a glass).

Referring to FIG. 1, the feeding assistance apparatus 10 is shown having the utensil 11 as effector, and as supported on the ground 12. The expression ground 12 is used in a generic manner, and may include any structure upon which the feeding assistance apparatus 10 may be mounted, such as a table, bar, chair, dedicated structure, a turntable as described hereinafter. The feeding assistance apparatus 10 may have its own base as well, as described in further detail hereinafter.

The movement assistance apparatus 10 is defined by a mechanism of links, interconnected in a particular manner to impose orientation-preserving constraints to the effector 11. For the simplicity of the present disclosure and to facilitate the description, the movement assistance apparatus 10 is described below as being generally divided into two linkage groups, namely a main arm 20 and a constraining mechanism 30. However, this is one way among others to describe the movement assistance apparatus 10, and is not an indication that the main arm 20 and constraining mechanism 30 are separated and/or independent organs. The movement assistance apparatus 10 is an integral assembly of collaborating links.

Main Arm 20

The main arm 20 may be viewed as the skeleton of the feeding assistance apparatus 10, as it will support the effector 11 and the other links thereon, such as those of the constraining mechanism 30. The main arm 20 has a base link 21 pivotally connected to the ground 12 at G1. A spacing link 22 is pivotally connected to the base link 21 at J1. A pivot F1 is at the effector end of the spacing link 22. Therefore, the base link 21 imposes a constraint to the movement of the spacing link 22 relative to the ground 12. As explained hereinafter, a degree of actuation (or damper) may be provided at G1 to cause reciprocating movement of the base link 21 relative to the ground 12.

For the sake of clarity, the present disclosure use a specific nomenclature to refer to the pivot joints of the movement assistance apparatus 10. Joints G (e.g., G1, G2, . . . ) are between the ground 12 and the movement assistance apparatus 10. Joints J (e.g., J1, J2, . . . ) are between interconnected links of the movement assistance apparatus 10, though with joints F (e.g., F1) being at the effector end of the movement assistance apparatus 10. The expression "link" is used herein to describe a rigid member, without in and of itself any degree of freedom between its ends. A link may be connected to another link by a joint. The expression "link assembly" to describe an arrangement of two or more links interconnected by one or more joints.

The movement of the spacing link 22 is consequently affected by the movement of the base link 21 via the shared pivot J1. The movement of the spacing link 22 is also driven by another link assembly, illustrated as having two links in FIG. 1, namely drive link 23 and drive link 24. The drive link assembly made of links 23 and 24 may be optional. There may be more than the two drive links 23 and 24 in the link assembly between the ground 12 and the spacing link 22. As illustrated, the drive link 23 may be pivotally connected to the ground 12 at G2. As an alternative, the drive link 23 may be connected to the ground by a translational joint, The drive links 23 and 24 are pivotally interconnected at J2, and the drive link 24 is pivotally connected to the spacing link 22 at J3. It is shown that J3 is on a portion of the spacing link 22 extending beyond pivot J1 (base link 21) away from the effector end (an extension). This may ensure that G1 and G2 are in close proximity to one another. For example, G1 and G2 may be coaxial as shown in an embodiment (e.g., as in FIGS. 7 and 8, though this is not necessary. J3 may also be between J1 and F1 (as in FIGS. 7 and 8). As explained hereinafter, a degree of actuation may be provided at G2 to cause reciprocating movement of the drive link 23 relative to the ground 12, for instance in the form of a motor or a linear actuator. The movements of the drive link 23 will entrain the rest of the linkage assembly, i.e., the drive link 24 in FIG. 1, resulting in movements of the spacing link 22 relative to the base link 21. The combined movements of the base link 21 and the drive link 23 may be controlled (or damped) to cause or constrain the utensil 11 to a desired range of movement along the X-Z plane.

The sizing of the links of the main arm 20 and the positioning of the pivot joints between components are selected as a function of the volume of movement for the utensil 11. For example, the components of the main arm 20 may be scaled up for tall adult users or scaled down for children users.

Constraining Mechanism 30

Still referring to FIG. 1, the constraining mechanism 30 is provided to impose orientation-preserving constraints to the effector 11 through movements of the effector 11 as driven by the main arm 20. The constraining mechanism 30 has a base link 31 pivotally connected to the ground 12 at G3. The base link 31 of the constraining mechanism 30 is parallel to the base link 21 of the main arm 20.

A spacing link 32 is indirectly connected to the base link 31 via a joining link 33, and extends to the effector end of the feeding assistance apparatus 10. The spacing link 32 of the constraining mechanism 30 is parallel to the spacing link 22 of the main arm 20.

The joining link 33 is shown having a triangular shape in FIG. 1. It may also have other shapes, such as a V shape, a three tier shape, etc. In another embodiment, there are more than one joining links 33, such as one link between J4-J1-J5, and another between J4-J5. The joining link 33 is pivotally mounted to the spacing link 22 of the main arm 20 at joint J1. Therefore, joint J1 defines the rotational axis for three links, i.e., the base link 21 and the spacing link 22 of the main arm 20, and the joining link 33. The joining link 33 is also pivotally connected to the base link 31 by joint J4, and is pivotally connected to the spacing link 32 by the joint J5. The joining link 33 serially connects the base link 31 and the spacing link 32 by having a rigid body. Stated differently, the movements of the base link 31 and of the spacing link 32 are tied by the presence of the joining link 33 between them. The joining link 33 is one embodiment of a serial interconnection between two 4-bar parallelograms of the present disclosure.

An effector link 34 is at the effector end of the movement assistance apparatus 10. The effector link 34 is pivotally connected to the spacing link 22 of the main arm 20 by joint F1. The effector link 34 is also pivotally connected to the spacing link 32 by joint F2. In the movement assistance apparatus 10 is a feeding assistance apparatus, the effector link 34 may have a utensil mount 35, such as a clamp, a loop, a hook, a gripper or any other component to hold a utensil or other feeding component. The utensil mount 35 is rigidly connected to the effector link 34, so as to move concurrently with it. An orientation adjustment may be present to adjust the orientation of the utensil mount 35 before locking it into place on the effector link 34. Although not shown, the effector link 34 could support any other independent mechanism, such as a rotational gripper that could allow a glass to be tipped. Moreover, the effector link 34 could be disconnected from the spacing link 22 if it is desired to change an orientation of the utensil 11.

The links of the constraining mechanism 30 are sized to form two 4-bar parallelograms with the links of the main arm 20. These two 4-bar parallelograms are serially connected by the joining link 33. A 4-bar parallelogram is defined as having four edges, with opposite edges being of a same length, and with the opposite edges remaining parallel at all times, through deformation of the parallelogram.

A first of the 4-bar parallelograms is defined by its four corners G1, G3, J4 and J1. Consequently, the four bars (a.k.a., links) forming the parallelogram are the ground, the base link 31, the joining link 33, and the base link 21. This may require a spacer to be present on the ground 12 to raise G3, as shown hereinafter.

A second of the 4-bar parallelograms is defined by its four corners J1, F1, F2, and J5. Consequently, the four bars (a.k.a., links) forming the parallelogram are the spacing link 22, the effector link 34, the spacing link 32 and the joining link 33.

The joining link 33 is consequently shared by the two 4-bar parallelograms, and therefore serially connects the two 4-bar mechanisms. As a result, this constrained connection between the ground 12 between G1 and G3, the joining link 33 and the effector link 34 maintains a constant orientation between them. Consequently, the orientation of the effector link 34 is fixed relative to the ground 12 at least in two rotational degrees of freedom, i.e., about axes X and Y, and possibly about axis Z if the movement assistance apparatus 10 is anchored immovably to the ground.

Range of Movement

Figure 2:
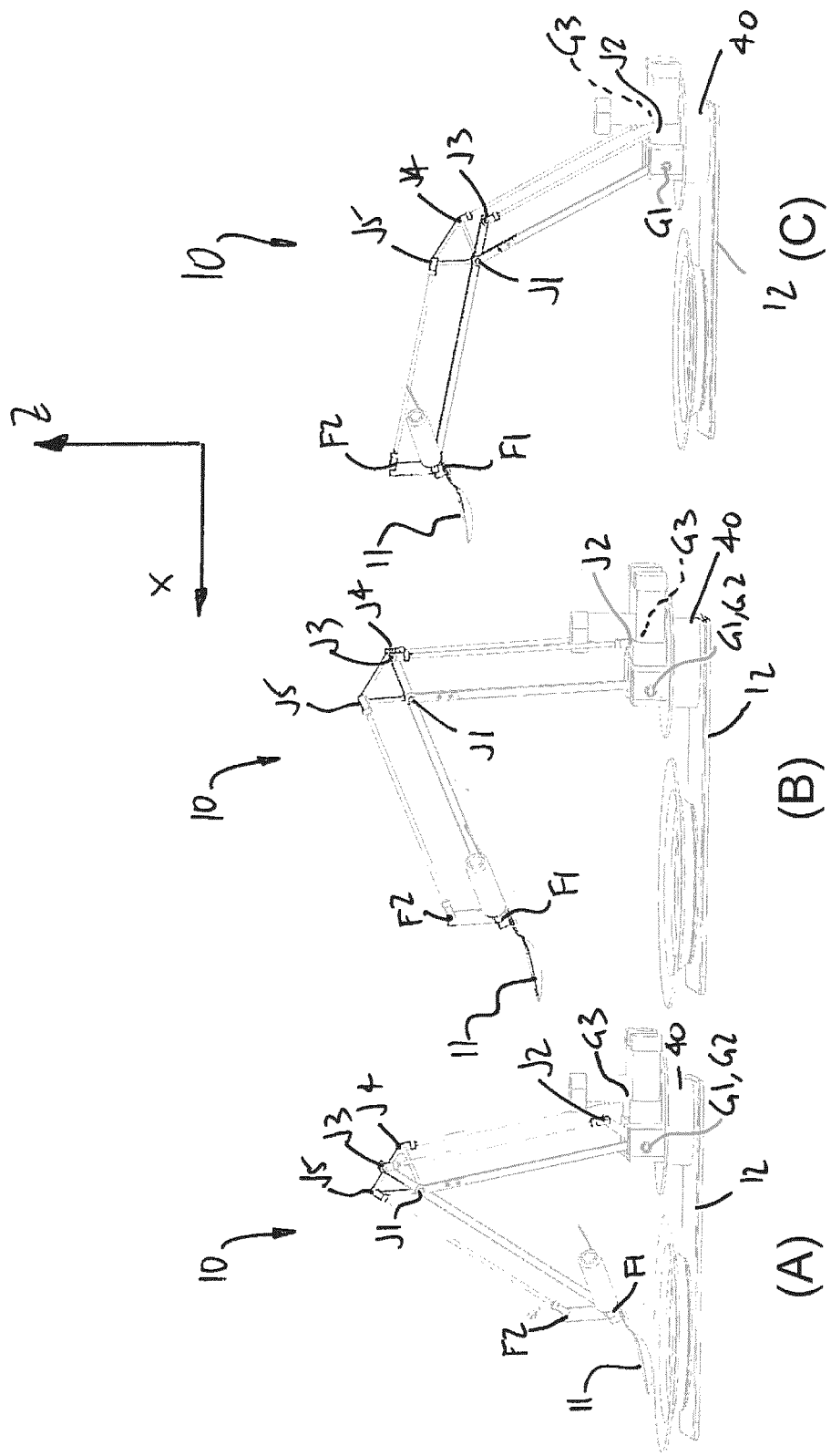
FIG. 2 is an illustration of a sequence of movements (A), (B), (C) of an effector mounted to the feeding assistance apparatus of FIG. 1.

Referring to the sequence (A), (B) and (C) of FIG. 2, there is shown the resulting movement constraints for the feeding assistance apparatus 10 as caused by the arrangement of the main arm 20 and the constraining mechanism 30. It is also observed from FIG. 2 that additional ground mounted components are present, such as motors, as described hereinafter. For simplicity, and to focus on the constant orientation, numerous reference numerals are absent from FIG. 2. However, the corners of the 4-bar parallelograms are shown for ease of understanding.

In (A), the feeding assistance apparatus 10 has guided the utensil 11 to a bowl, to scoop some of the content from the bowl. In (B), the utensil 11 is in an intermediate position, on its way to a user's mouth. In (C), the utensil 11 is in a feeding position, where the utensil 11 can be reached by one's mouth. The feeding position of (C) may be farther out, by a sizing of the main arm 20 and of its drive link assembly (e.g., drive links 23 and 24). The reverse sequence of movements may then be performed, from (C) to (B) to (A), to scoop additional bowl content.

As observed, throughout (A), (B), (C), the utensil 11 maintains a constant orientation about axes X, Y and Z. It may be possible for the feeding assistance apparatus 10 to rotate about axis Z as the feeding assistance apparatus 10 may be on a turntable 40. The turntable 40 may support the main arm 20 and the constraining mechanism 30 by having pivots G1, G2 and G3 anchored on a top surface 41 thereof. The turntable 40 may also have a base (now shown) laid on the ground (i.e., table, structure), with a rotational joint between the top surface 41 and the ground. An axis of the rotational joint may extend along axis Z, such that the utensil may rotate about axis Z while maintaining its horizontality.

Actuation of the Feeding Assistance Apparatus 10

The feeding assistance apparatus 10 of the present disclosure may be used as shown as in FIG. 1. The feeding assistance apparatus 10 of FIG. 1 may hence support a utensil 11 in constant orientation despite user conditions such as hand tremors, spasms, shakes. The inertial of the components of the feeding assistance apparatus 10 and inherent joint friction may filter out vibrations from the hand tremors of a user manipulating the utensil 11. The feeding assistance apparatus 10 may feature friction adjustment to one or more of the joints, to set a desired amount of resistance to movements for the feeding assistance apparatus 10, again in an effort to isolate the utensil from tremors or like user conditions (such as dampers and motors).

It is nonetheless possible to provide actuators for the feeding assistance apparatus 10, notably with a controller or like processing unit that may be actuated by touch buttons to effect the movements of FIG. 2. Therefore, by touch buttons or like electronic commands (e.g., voice actuation, "up", "down"), the feeding assistance apparatus 10 may be actuated through its movements of FIG. 2.

Referring to FIG. 3, a pair or mounts 50 are shown, respectively to support shafts 51 forming parts of joints G1 and G2. For compactness of the arrangement, the axes of rotation of the shafts 51 at G1 and G2 are coaxial, although this is an optional embodiment. Springs may be mounted to the shafts 51 in order to balance the weight of the main arm 20 for the main arm 20 to maintain any orientation in spite of gravity. Springs may also be used to bring the main arm 20 to predetermined orientations. Such springs could be active or passive springs. According to an embodiment, a biasing mechanism featuring springs may be coupled or decoupled to the main arm 20 (e.g., mechanically, electrically, electro-mechanically) for example via shafts 51, to cause a movement to any orientation, such as the end positions of FIG. 2A or of FIG. 2C, Reverse movements can be achieved (from FIG. 2A to 2C, or from FIG. 2C to 2A) with such biasing mechanisms.

Referring to FIG. 4, actuators 60 are provided to actuate the rotation of the joints G1 and G2. An actuator could also be provided for G3. In an embodiment, the actuators 60 are reciprocating electric motors, aka., bidirectional motors. As explained above, it is possible to use other types of actuators, such as a linear actuator notably as an alternative to the rotational actuation at G2. In FIG. 4, the actuators 60 have their shafts transverse to the shafts 51, and are coupled to the shafts 51 by way of gear assemblies 52 in the mounts 50, however, this is only an option among others. According to an embodiment, the gear assemblies 52 include bevel gears, and the gear assemblies 52 perform gear reduction to increase the torque from the actuators 60 to the shafts 51. An additional actuator 70 has its shaft vertical, i.e., extending along axis Z, and is used to control rotation of the turntable 40. The actuators 60 and 70 (if present) may be driven by a common controller 75 (a.k.a., a processing unit) that controls the actuator input for the utensil 11 to be moved at a desired velocity, and in a predetermined path of movement, such as the sequence (A)-(B)-(C) of FIG. 2. As the actuators 60 may be reciprocating motors, the action of the controller 75 may be necessary to ensure appropriate concurrent input from the actuators 60 and 70. This may entail the use of sensors (e.g., accelerometers), movement sensors, encoders, strain gauges, etc, at various locations on the movement assistance apparatus 10. One such sensor is shown at 75' in FIG. 4.

It is also contemplated to use the actuators 60 and 70 (if present) as movement absorbers, as opposed to using them to raise and lower the main arm 20. The actuators 60 and 70 would be used as actuatable dampers. In such an embodiment, the actuators 60 and 70 may be DC motors, stepper motors, magnetorheological fluid actuators, etc. As another alternative, items 60 and 70 can be passive dampers as well, that would not require any active control. With sensors 75' appropriate placed, the controller 75 may detect unwanted movements of the movement assistance apparatus 10, for example as a result of hand tremor, spasms, etc. The controller 75 may employ different approaches to provide its actuation commands, based on feedback from the sensors 75'. According to an embodiment, the controller 75 has a normally-off movement absorption mode in which the actuators 60 and 70 of the movement assistance apparatus 10 do not produce inertia or movement absorption unless unwanted movements are detected (e.g., vibrations resulting from tremor or spasms) via readings from the sensors 75'. If the movements from the user are smooth, fluid, continuous, the movement assistance apparatus 10 may not intervene with an actuated output. According to another embodiment, the controller 75 has a normally-on movement absorption mode in which the actuators 60 of the feeding assistance apparatus 10 produce inertia and/or movement absorption unless movements from the user are detected to be smooth, fluid, continuous. The actuators 60 and 70 (if present) may be driven to offset any such unwanted movements, or to oppose forces to unwanted movements. For example, using the readings from the sensor(s) 75', the controller 75 may determine from the frequency, magnitude and/or amplitude of forces applies to the movement assistance apparatus 10 that some parts of the forces are unwanted, such movements result from spasms, tremor, dyspraxia, and filter them out for the effector 11 (e.g., utensil, pen, or other tool) not to effect such unwanted movements. The actuators 60 and 70 can also concurrently be used to constrain the possible movement to a given path in spite of unwanted forces applied to the movement assistance apparatus 10.

A system for movement assistance of an effector may include the movement assistance apparatus 10 in accordance with any of the embodiments described herein, along with the controller 75 or like processing unit, and sensor(s) 75'. The system may further include a non-transitory computer-readable memory communicatively coupled to the processing unit and comprising computer-readable program instructions executable by the processing unit for obtaining and interpreting the signals; identifying unwanted forces applied to the apparatus from the signals; and driving the first actuator and the second actuator for the effector link to move without movements caused by the unwanted forces or to offset the unwanted forces; driving the first actuator and/or the second actuator to assist in moving the apparatus; and/or driving the first actuator and/or the second actuator to create inertia in the apparatus.

Figure 5:
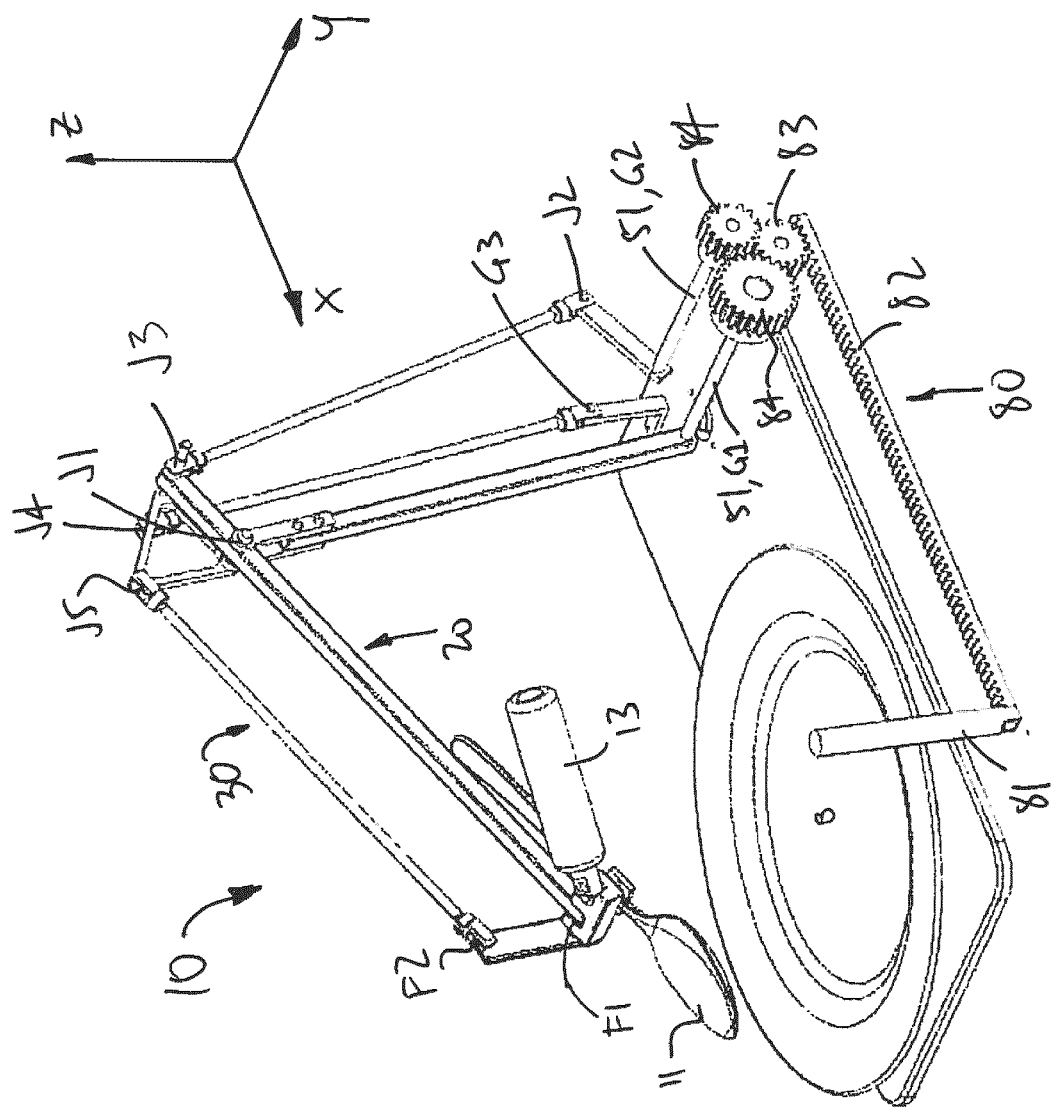
FIG. 5 is a perspective view of the feeding assistance apparatus of FIG. 3, with an exemplary manual driving mechanism.

Referring to FIG. 5, in accordance with another embodiment, there may be provided a manual driving mechanism 80 for a user to manually control the movements of the feeding assistance apparatus 10, for instance according to the sequence (A)-(B)-(C) of FIG. 2. The manual driving mechanism 80 may be suited for users who have limited range of arm movements for instance due to injury or ailments or to insufficient muscular force. The manual driving mechanism 80 may be used with a user having an arm rested on a table, with a simple back and forth (or left and right) hand movement. The mechanism 80 could take other forms, i.e., not only gears, but tendons and pulleys, etc.

The manual driving mechanism 80 may feature a handle 81 at the end of a rack 82. Although not shown, the rack 82 may be mounted to a carriage or rail to translate in a reciprocating manner as a result of a manual handling of the handle 81. A pinion 83 is meshed with the rack 82 to convert a translation of the rack 82 into a rotation. The pinion 83 is meshed with gears 84, respectively connected with the shafts 51. The rotation of the pinion 83 is therefore distributed to the gears 84 that will transmit the rotation to the base link 21 and to the drive link 23. Therefore, by a single degree of actuation, i.e., the reciprocating movement of the rack 82, the utensil 11 may be moved according to the sequence (A)-(B)-(C) of FIG. 2. While the arrangement of FIG. 5 is shown with manual actuation, it is contemplated to have the pinion 83 mounted to a motor shaft, for a single motor to operate the feeding assistance apparatus 10 in the manner described above.

Therefore, the movement assistance apparatus 10 can be generally described as an apparatus comprising: a main arm having links extending from a ground end to an effector end and actuatable or dampable for movement of the effector end from a first position to a second position, the links including a base link adapted to be pivotally mounted to a ground, and a spacing link pivotally mounted to a free end of the base link and extending to the effector end; a first 4-bar parallelogram having pivot joints at its corners and including the base link of the main arm; a second 4-bar parallelogram having pivot joints at its corners and including the spacing link of the main arm and an effector link adapted to support an object. The first 4-bar parallelogram and the second 4-bar parallelogram are serially interconnected whereby the effector link is constrained to maintaining a constant orientation in at least two rotational degrees of freedom. In an embodiment, the 4-bar parallelograms lie in a plane that is transverse, and possibly perpendicular, to a plane of the ground 12 (e.g., FIG. 1). In another embodiment, the 4-bar parallelograms lie in a plane that is parallel to a plane of the ground 12 (e.g., FIG. 7).

Figure 6:
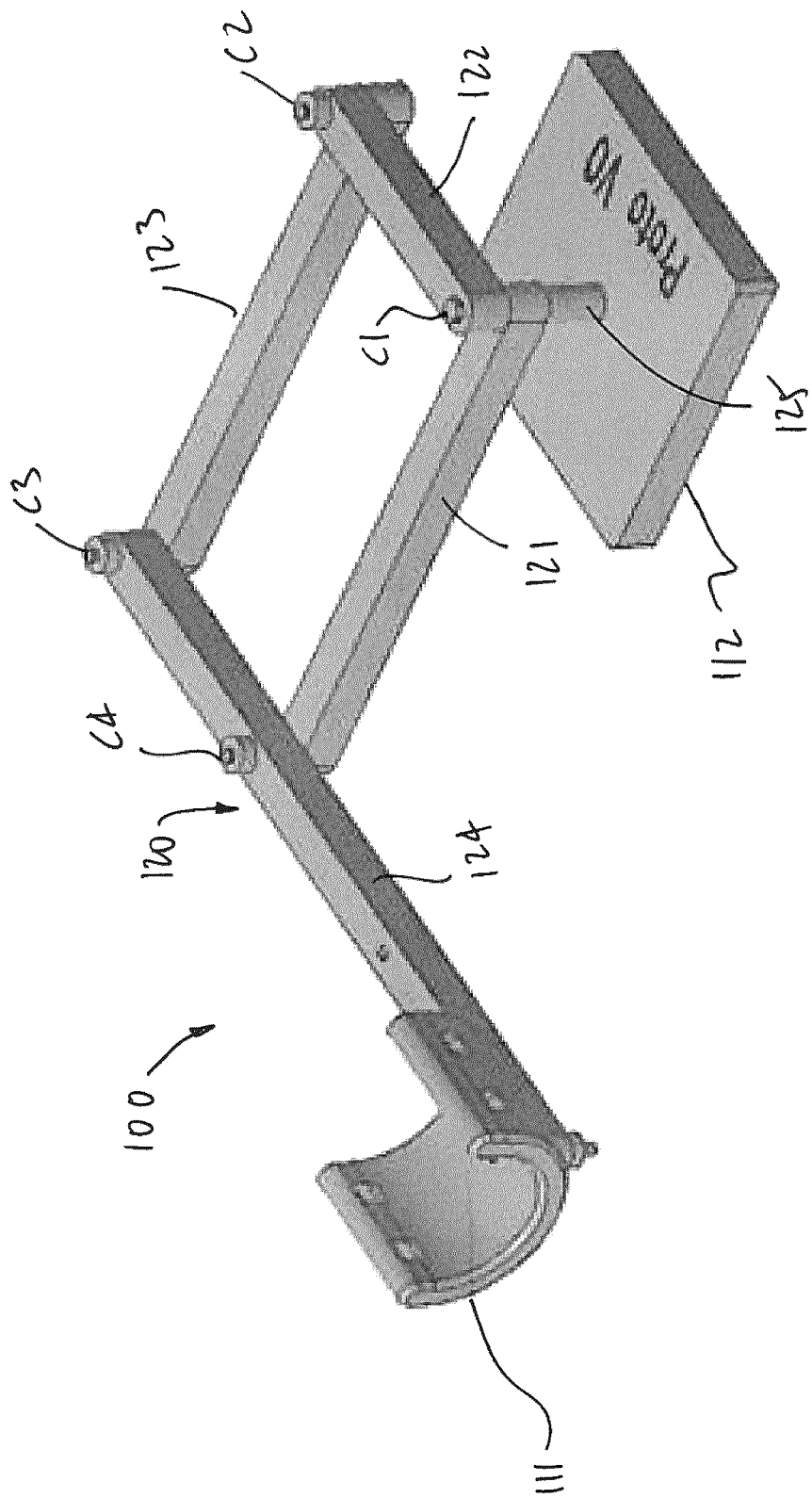
FIG. 6 is a perspective view of a movement assistance apparatus in accordance with another embodiment of the present disclosure.

Referring to FIG. 6, there is illustrated another assistance apparatus 100. The movement assistance apparatus 100 is of the type that may be used to support a user's limb and/or stabilize his/her movements during an action, such as when a user wants to write. The movement assistance apparatus 100 operates in planar movements. According to an embodiment, the movement assistance apparatus 100 is used with a support 111 such as a U-shaped arm support as in FIG. 6, with the support 111 maintaining a constant orientation relative to the ground 112, and a constant distance relative to a plane parallel to an arm 120 of the apparatus 100. Any other type of support or tool may be at the end of the arm 120 of the apparatus 100. Again, the expression "ground" is used generically to represent a surface, mechanism or structure supporting the movement assistance apparatus 100. The "ground" may for example be a table, a wheelchair, and may also include mechanisms such as a turntable described above.

The arm 120 is a 4-bar parallelogram that is defined by its four corners C1, C2, C3 and C4, with four links shown as 121, 122, 123 and 124. A shaft 125 interfaces the parallelogram to the ground 12, and is at corner C1, between links 121 and 122. Link 124 is a spacing link having the support 111 at its effector end. The arrangement of FIG. 6 may be compact in that all actuation and/or damping may be at the ground 112, whereby a controller may provide all of its input via the shaft 125. In the arrangement of FIG. 6, an axis of the shaft 125 is normal to a plane of deformation of the 4-bar parallelogram and may also be normal to the ground 112.

Figure 7:
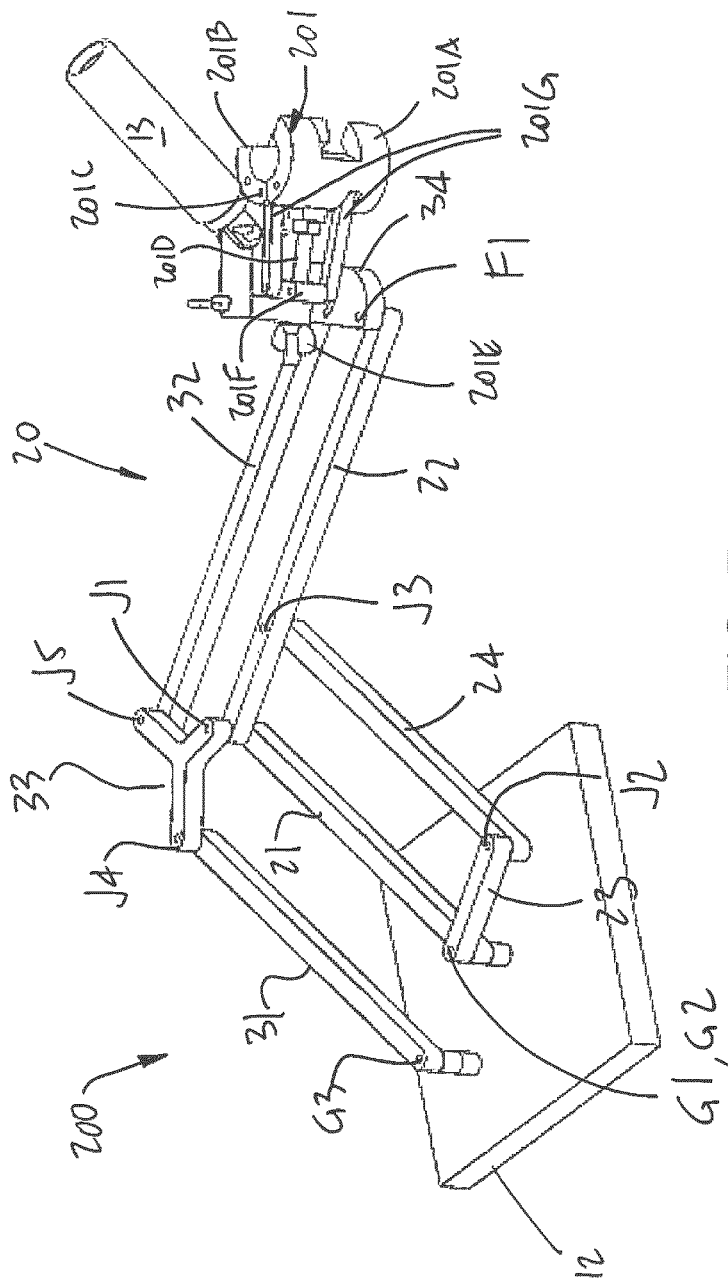
FIG. 7 is a perspective view of a writing assistance apparatus in accordance with the present disclosure.
Figure 8:
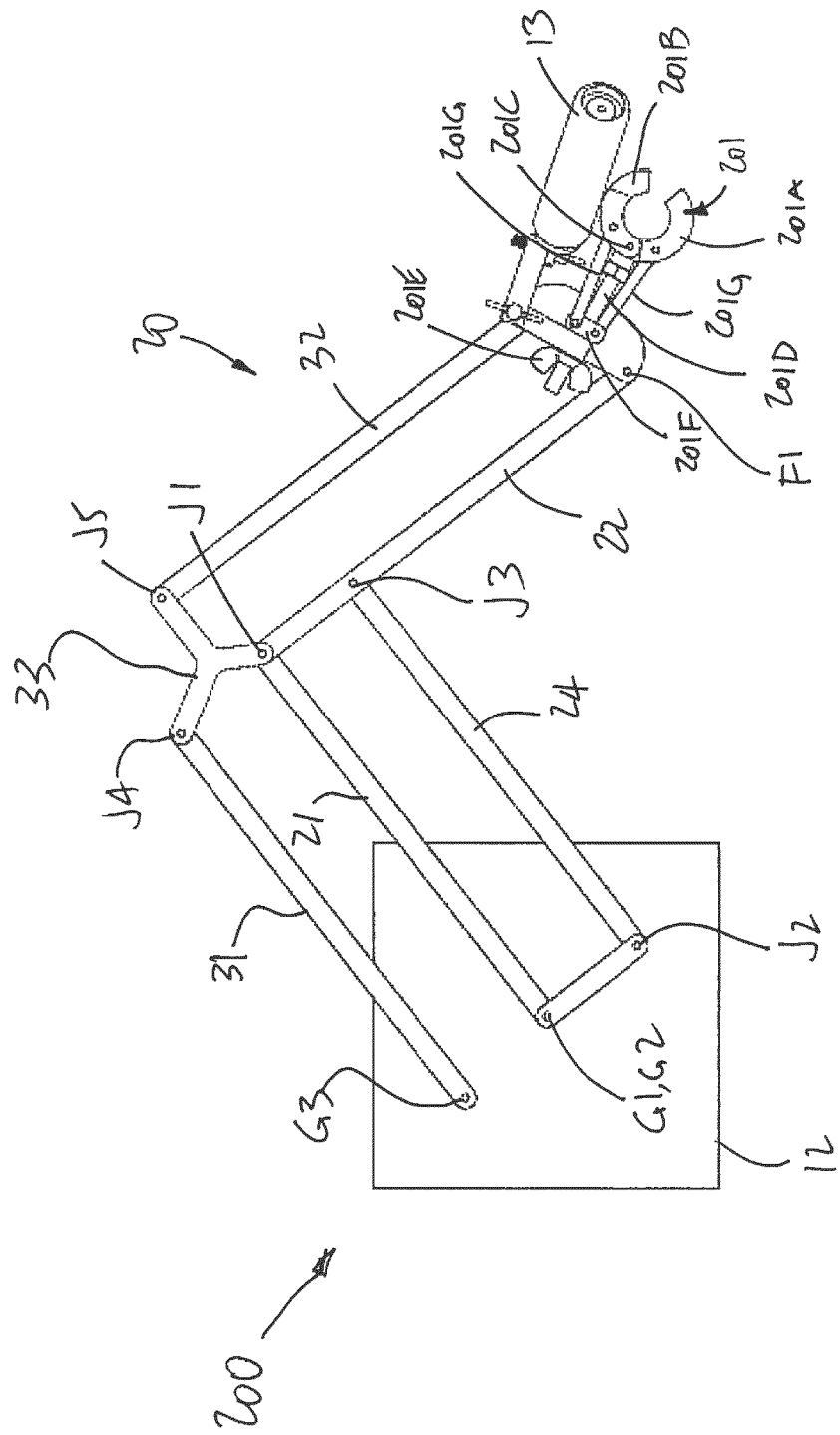
FIG. 8 is a top plan view of the writing assistance apparatus of FIG. 7.

Referring to FIGS. 7 and 8, there is illustrated another configuration of the movement assistance apparatus 10, in the form of a writing assistance apparatus 200. The writing assistance apparatus 200 is of the type that may be used to hold a pen, pencil, or like writing instrument, for the writing instrument to be stabilized when a user manipulates the writing assistance apparatus 200 to write, draw, paint, etc. The writing assistance apparatus 200 operates in planar movements, with a writing tip of the writing instrument moving in a plane that is generally parallel to that of a table supporting a sheet, canvas, substrate, etc. The writing assistance apparatus 200 has the same linkage and joint arrangement as that of the feeding assistance apparatus 10 of FIG. 1, whereby like components will bear like reference numerals and letters. In the writing assistance apparatus 200, J3 is shown as being between J1 and F1, though it may also be at the end of the spacing link 22. Moreover, G1 and G2 are shown as being coaxial, yet they may be parallel and not co-axial as well.

In order to hold a writing instrument, the writing assistance apparatus 200 may have any appropriate type of writing instrument interface, such as a clamp, holder, fastener. For example, a resilient clamp may be used. In FIGS. 7 and 8, another embodiment of the clamp is shown at 201, and is in the form of a C-shaped clamp. The C-shaped clamp 201 has a pair of pivotally connected clamp portions 201A and 201B, connected at pivot 201C. A lengthening bolt 201D and nut 201E may cause a central slider 201F to slide along the bolt 201D. The movement of the central slider 201F along the bolt 201D rotates the legs 201G which will consequently being the clamp portions 201A and 201B toward or away from one another. This is one configuration among others, as more simple solutions could be used as well, such as a set screw in a tubular holder, etc. According to an embodiment, a biasing mechanism featuring springs may be coupled or decoupled to the arm 20 (e.g., mechanically, electrically, electro-mechanically), to cause a movement to any orientation.

The writing assistance apparatus 200 may be movable out of plane, for a user to raise the writing instrument and separate it from a writing surface. In an embodiment, the out-of-plane movement may be enabled by the elastic deformation of the mechanism, considering that the C-shaped clamp 201 is cantilevered distally from the ground 12. Alternatively, or additionally, a mechanism or deformable member may be present to facilitate the out-of-plane movement.

Referring to FIGS. 9-12, the movement assistance apparatus 10 is shown supporting the utensil 11 with different components in comparison to the feeding assistance apparatus 10 of FIG. 1. The main arm 20 and the constraining mechanism 30 are generally similar between FIG. 1 and FIGS. 9-12, whereby like numerals will refer to like components. Moreover, for clarity of the figures, some reference numerals have been left out from FIGS. 9 and 10.

As observed from FIGS. 9 and 10, the handle 13 may be connected directly to the spacing links 22 and 32, via a link 13A (e.g., a handle link). The link 13A may be joined to the links 22 and 32 by rotational joints as shown at H1 and H2. The segment of the link 13A between H1 and H2 may consequently be parallel to the segment F1 and F2 (a.k.a., side or bar), and also parallel to the segment J1-J5 (a.k.a., side or bar). The segment H1-H2 may form for example a sub parallelogram (a 4-bar mechanism within the 4-bar mechanism defined by J1-F1-F2-F5), such as H1-H2-F2-F1, or H1-H2-J5-J1. In an embodiment, various hole pairs may be defined in the spacing links 22 and 32 to allow a user to position the link 13A in a desired position, whether closer or farther to the utensil 11. The link 13A may further include a bracket portion 13B to which the handle 13 may be connected. The bracket portion 13B orients the handle 13 away from a plane of the 4-bar mechanism defined by J1-F1-F2-F5. In an embodiment, the bracket portion 13B is transverse, e.g., at 90 degrees from the plane of the 4-bar mechanism defined by J1-F1-F2-F5. The handle 13 may be detachably connected to the bracket 13B, for its angle to be adjustable. By having the handle 13 located between the effector 11 and pivot points J1 and J5, the movement of the effector 11 will be amplified in amplitude relative to movement applied to the handle 13. Stated differently, for a movement of an arbitrary distance D applied to the handle 13, the effector 11 may move by a distance of 1.2 D, for example. The user is thus required to do a smaller movement than the resulting movement of the effector 11, resulting in a reduced amplitude of movement by the user: the user may not need to raise his/her arm as much.

Figures 11, 12:
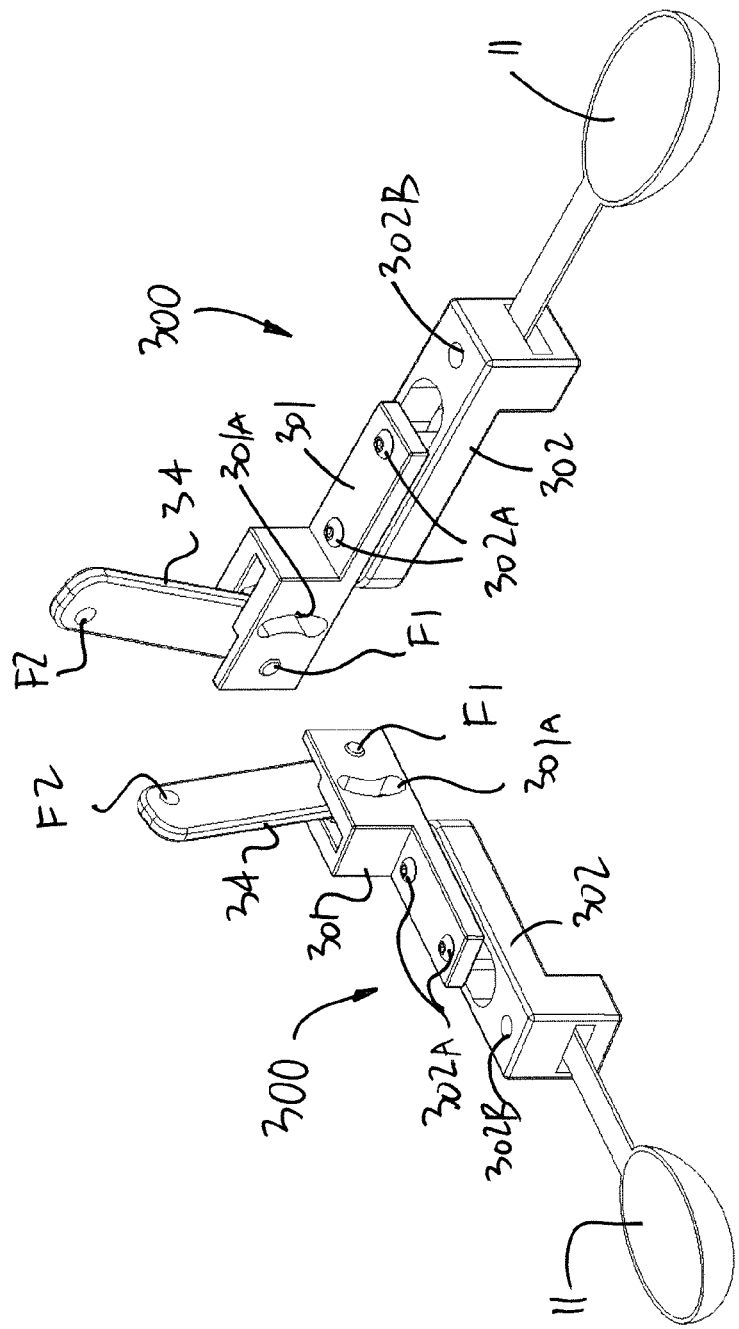
FIG. 11 is a first perspective view of the utensil interface of FIG. 9.
FIG. 12 is a second perspective view of the utensil interface of FIG. 9.

Referring to FIGS. 11 and 12, a utensil interface is generally shown at 300. The utensil interface 300 supports a spoon 11, but other utensils or devices may be held by the interface 300. The interface 300 is connected to the effector link 34, shown in FIGS. 11 and 12 as detached from the apparatus 10. The interface 300 may be connected to the joint F1, though it may also be connected to other parts of the effector link 34, including joint F2.

The interface 300 may have a base link 301. The base link 301 may be connected to the effector link 34 by a lockable rotational joint. This enables a user to rotate the base link 301 relative to the effector link 34 to a desired orientation, to then lock such orientation. Various possible mechanisms could achieve the locking, including an indexing mechanism. Arcuate slots 301A are shown in the base link 301, and may receive a fastener (e.g., bolt, set screw) to lock the base link 301 in a selected orientation relative to the effector link 34.

A support link 302 may be connected to the base link 301 by way of a lockable translational joint, closable by set screws 302A or equivalent (e.g., indexing mechanism, bolts, etc). The lockable translational joint (or telescopic joint, sliding joint) may be used to adjust a distance between the effector link 34 and the utensil 11. The utensil 11 may be received in a free end of the support link 302. In an embodiment, a set of interchangeable utensils 11 or tools is provided (e.g., different spoon sizes, fork, knife, pencil and pen) to be replaced at the end of the support link 302. The utensil(s) 11 may be connected to the support link 302 by a fastener 302B or like lockable pivot that may allow an orientation of the utensil 11 relative to the support link 302 to be adjusted. According to an embodiment, a damping component may be between the base link 301 and the support link 302, or between the support link 302 and the utensil 11. The damping component may be a rubber pad or spacer, or like elastomeric material. Therefore, the utensil 11 may be resiliently connected to the movement assistance apparatus 10, to have some give in case of accidental contact, etc.

The invention claimed is:

1. An apparatus comprising:
   a main arm having links extending from a ground end to an effector end and allowing movement of the effector end from a first position to a second position, the links including at least a base link adapted to be pivotally connected to a base, and a spacing link pivotally mounted to a free end of the base link and extending to the effector end;
   a first 4-bar parallelogram having pivot joints at its corners and including the base link of the main arm;
   a second 4-bar parallelogram having pivot joints at its corners and including the spacing link of the main arm and an effector link at the effector end adapted to support an object;
   a serial interconnection between the first 4-bar parallelogram and the second 4-bar parallelogram constraining the effector link to maintaining a constant orientation in at least two rotational degrees of freedom relative to the base; and
   a handle connected to the second 4-bar mechanism at a location being offset from the effector end and between the serial interconnection and the effector end such that an amplitude of a movement of the effector end is greater than an amplitude of a movement applied to the handle.

2. The apparatus according to claim 1, further comprising a drive link assembly between the spacing link of the second 4-bar mechanism and the base.

3. The apparatus according to claim 2, wherein the drive link assembly includes a first link and a second link pivotally interconnected to one another.

4. The apparatus according to claim 3, wherein the first link is pivotally connected to the ground, and the second link is pivotally connected to the spacing link.

5. The apparatus according to claim 4, wherein the first link and the base link are coaxially pivotally connected to the ground.

6. The apparatus according to claim 2, wherein a portion of the spacing link extends beyond one said pivot joint of the second 4-bar parallelogram, the drive link assembly being connected to said portion of the spacing link.

7. The apparatus according to claim 2, further comprising a first actuator operatively connected to the base link to actuate a pivot connection of the base link to the base.

8. The apparatus according to claim 7, further comprising a second actuator operatively connected to the drive link assembly to actuate a pivot connection of the drive link assembly to the base.

9. The apparatus according to claim 2, further comprising a manual driving transmission operatively connected to the base link to actuate a pivot connection of the base link to the base, and operatively connected to the drive link assembly to actuate a pivot connection of the drive link assembly to the base.

10. The apparatus according to claim 1, wherein the serial interconnection includes a single joining link forming a bar of the first 4-bar parallelogram and a bar of the second 4-bar parallelogram, and pivotally connected to a joint connecting the free end of the base link to the spacing link.

11. The apparatus according to claim 1, wherein a plane in which lies the first and second 4-bar mechanisms is transverse to the base.

12. The apparatus according to claim 1, wherein a plane in which lies the first and second 4-bar mechanisms is parallel to the base.

13. The apparatus according to claim 1, further comprising a turntable between the base and the ground.

14. The apparatus according to claim 1, further comprising a utensil connected to the effector link.

15. The apparatus according to claim 1, further comprising a handle link interfacing the handle to the second 4-bar mechanism.

16. The apparatus according to claim 15, wherein the handle link is pivotally connected to the second 4-bar mechanism and parallel to two bars of the second 4-bar mechanism.

17. The apparatus according to claim 16, further comprising a bracket portion on the handle link, the handle connected to the bracket portion.

18. The apparatus according to claim 17, wherein the bracket portion is transverse to a plane of the 4-bar mechanisms.

19. The apparatus according to claim 17, wherein the handle is rotatably connected to the bracket portion by a rotational joint.

20. An apparatus comprising:
    a main arm having links extending from a ground end to an effector end and allowing movement of the effector end from a first position to a second position, the links including at least a base link adapted to be pivotally connected to a base, and a spacing link pivotally mounted to a free end of the base link and extending to the effector end;
    a first 4-bar parallelogram having pivot joints at its corners and including the base link of the main arm;
    a second 4-bar parallelogram having pivot joints at its corners and including the spacing link of the main arm and an effector link at the effector end adapted to support an object;
    a serial interconnection between the first 4-bar parallelogram and the second 4-bar parallelogram constraining the effector link to maintaining a constant orientation in at least two rotational degrees of freedom relative to the base; and
    a drive link assembly between the spacing link of the second 4-bar mechanism and the base, the drive link assembly including a first drive link pivotally connected to the base and a second drive link pivotally connected to the first drive link, the second drive link pivotally connected to the spacing link.

* * * * *